United States Patent
Sato et al.

[11] Patent Number: 5,460,184
[45] Date of Patent: Oct. 24, 1995

[54] MENTAL-CONCENTRATION MEASURING METHOD AND APPARATUS

[75] Inventors: Toshiyuki Sato, Tokyo; George Sakamoto, c/o Gez Corporation No. 801, 1-11-2 Hiroo, Shibuya, Tokyo; Hirotoki Kawasaki, 1-4-8-201, Minamiazabu Minato-ku, Tokyo; Morikuni Takigawa, 3-6-8, Murasakibaru Kagoshima-shi, Kagoshima-ken, Tokyo, all of Japan

[73] Assignees: DFC Co., Ltd.; George Sakamoto, both of Tokyo; Morikuni Takigawa, Kagoshima; Hirotoki Kawasaki, Tokyo, all of Japan; a part interest

[21] Appl. No.: 106,903

[22] Filed: Aug. 13, 1993

[30] Foreign Application Priority Data

Aug. 19, 1992 [JP] Japan ................... 4-220186

[51] Int. Cl.$^6$ ........................................ A61B 5/048
[52] U.S. Cl. .................................................. 128/731
[58] Field of Search ............................... 128/731.2

[56] References Cited

U.S. PATENT DOCUMENTS 4,228,807 10/1980 Yagi et al. ........................... 128/732
4,800,895 1/1989 Moberg et al. ..................... 128/731
4,955,388 9/1990 Silberstein .......................... 128/731

Primary Examiner—Angela D. Sykes
Attorney, Agent, or Firm—McGlew and Tuttle

[57] ABSTRACT

A mental-concentration measuring method for measuring the degree of mental concentration of a subject by extracting a power spectrum with respect to a brain wave from detected brain-wave biological signals, obtaining an integrated value of the power spectrum and an integrated value of a rhythm spectrum representing mental concentration power, and measuring the mental concentration of the subject based on the ratio of these integrated values, and mental-concentration measuring apparatus as apparatus for realizing the above method comprising a brain-wave extracting device for extracting a power spectrum of a brain wave, a brain-wave spectrum integrating device for integrating the brain-wave power spectrum extracted by the brain-wave extracting device, an α-rhythm spectrum integrating device for integrating an α-rhythm spectrum representing mental concentration power, and a mental-concentration calculating device for calculating the ratio of the integrated value obtained with the α-rhythm spectrum integrating device and the integrated value obtained with the brain-wave spectrum integrating device.

6 Claims, 5 Drawing Sheets

MENTAL-CONCENTRATION MEASURING METHOD AND APPARATUS

FIELD OF THE INVENTION

This invention relates to a method and apparatus for extracting power spectrum from the biological signals of a brain wave, and measuring the mental concentration of a subject based on the ratio of a rhythm in the power spectrum.

BACKGROUND OF THE INVENTION

In recent years, various attempts have been made to know mental activities of human being by analyzing the brain wave of the human brain.

The past analyses and studies revealed that there are sinewave signals after or portions of the brain wave called α, β, δ and Θ rhythms, any one of which is generated or amplified in accordance with the state of mind of an individual person at the time of measurement.

A frequency component of a brain wave ranging from 0.5 Hz to 3.5 Hz is called the δ rhythm, that ranging from 3.5 Hz to 7.5 Hz the Θ rhythm, that ranging from 7.5 Hz to 13.5 Hz the α rhythm, and that ranging from 13.5 Hz to 30.5 Hz the β rhythm, respectively.

As means for studying the mental activities of human being, attempts have also been made to analyze the brain wave and measure the degree of mental concentration based on the α rhythm in the brain wave.

A means for detecting the aforementioned α, β, δ and Θ rhythms has already been proposed by some of the present Applicants (U.S. Patent application Ser. No. 07/794,526). As a means for extracting the α rhythm of this invention, which will be described later, the means used in the invention for which the aforementioned application was filed may be used as it is.

Conventional mental-concentration measuring methods usually rely upon electrodes pierced into the head of a subject for extracting a signal component representing the α rhythm alone from among small biological signals generated on the electrodes, and measure the mental concentration of the subject based on an absolute amount obtained by integrating the potentials thereof.

With these conventional methods, however, contact resistance between the electrode and the skin may greatly vary depending on the manner in which the electrodes are pierced into the head, or the state of the skin. As a result, the measured potentials may also vary even when measured simultaneously, as shown in curves A and B in FIG. 1, which are shown in a somewhat exaggerated manner. This could result in failure to precisely reflect the mental activities of human being.

SUMMARY OF THE INVENTION

This invention is intended to solve the aforementioned shortcomings. It is an object of this invention to provide a method and apparatus for measuring mental concentration based on the ratio of α rhythm to the whole brain wave without being affected by measuring environments, including the manner in which the electrodes are pierced into the head.

BRIEF DESCRIPTION OF THE DRAWINGS

FIG. 8 is a flow chart of the processing steps in an embodiment of this invention.

DETAILED DESCRIPTION OF THE EMBODIMENTS

Figure 1:
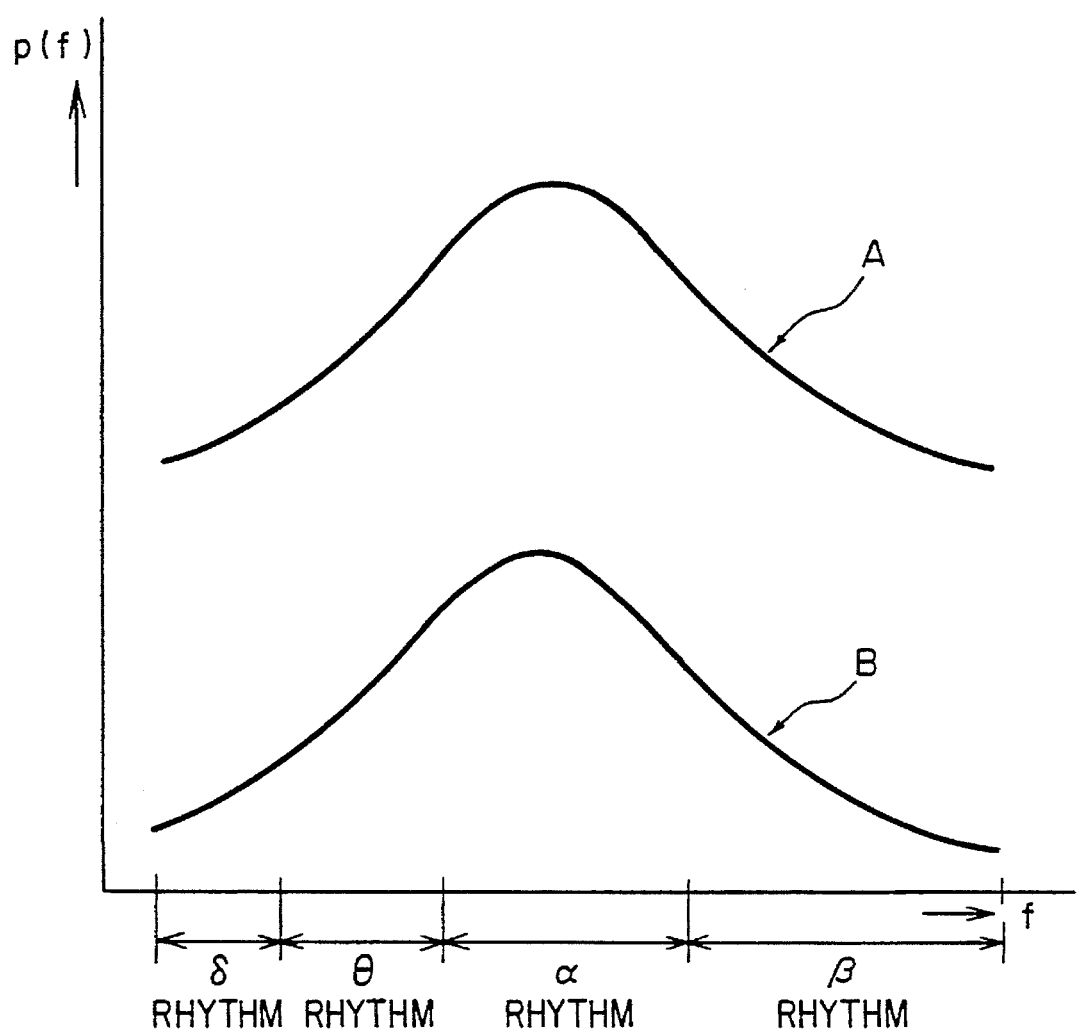
FIG. 1 is a diagram in which brain waves obtained in different states of electrode penetration are compared.
Figure 2:
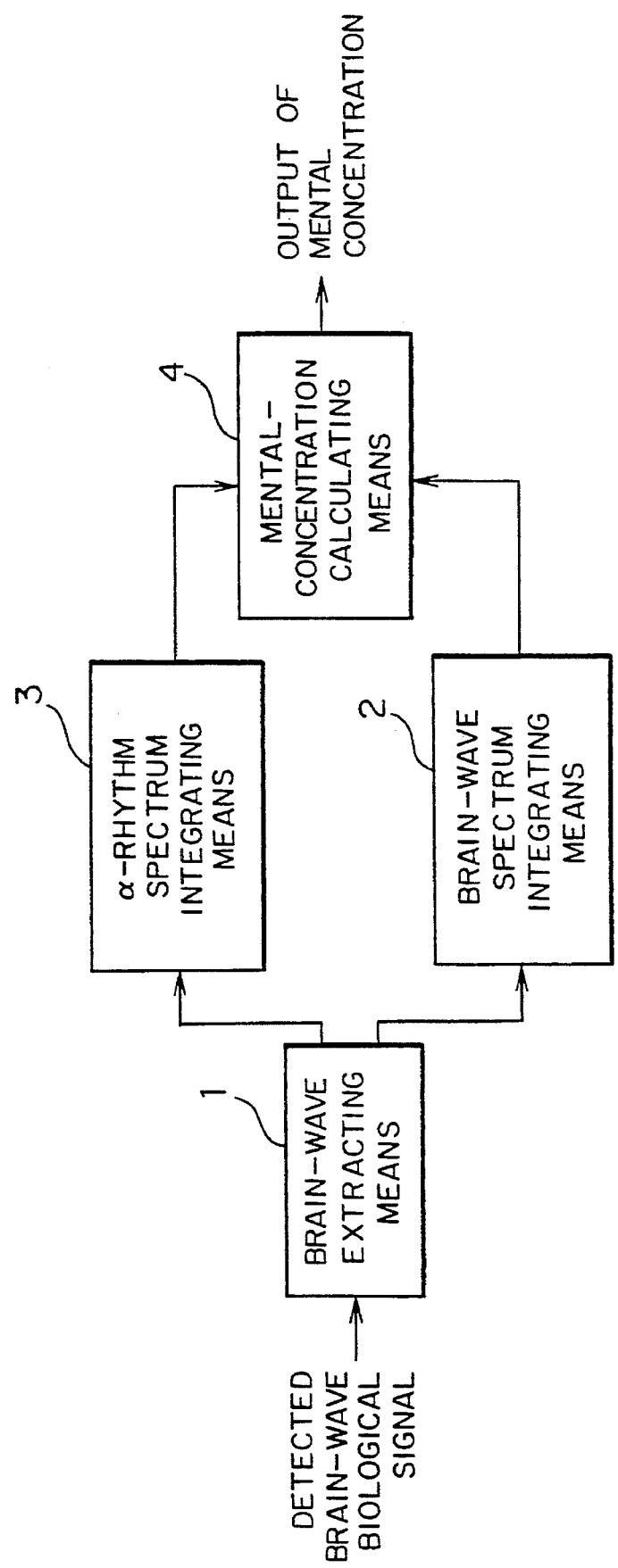
FIG. 2 is a diagram of assistance in explaining the operating principle of this invention.

FIG. 2 is a diagram of assistance in explaining the operating principle of this invention. In the figure, reference numeral 1 refers to a brain-wave extracting means; 2 to a brain-wave spectrum integrating means; 3 to an α-rhythm spectrum integrating means, and 4 to a mental-concentration calculating means, respectively.

The brain-wave extracting means 1 receives biological signals of a brain wave detected from the head of a subject, filters them in an analog or digital method to extract signal components of δ, Θ, α and β rhythms.

The brain-wave spectrum integrating means 2 integrates the potential of the spectrum of the whole signal components ranging from the δ rhythm to the β rhythm extracted by the brain-wave extracting means 1 so as to obtain the power of the brain wave.

Now, assuming that the spectrum of the brain wave extracted by the brain-wave extracting means 1 is p(f), the total brain-wave power $P_O$ can be expressed by the following equation.

$$P_0 = \int_{0.5}^{30.5} p(f) df. \quad (1)$$

The α-rhythm spectrum integrating means 3 is for obtaining the power of the a rhythm by integrating the potentials of the spectrum of the α-rhythm signal component among the signal components ranging from the α rhythm to the β rhythm extracted by the brain-wave extracting means 1.

Assuming that the power of the α rhythm is $P_\alpha$, $$P_\alpha = \int_{7.5}^{13.5} p(f) df. \quad (2)$$

The mental-concentration calculating means 4 is for calculating the ratio $P_\alpha P_O$ of the power α-rhythm $P_\alpha$ of the α rhythm obtained by the α-rhythm spectrum integrating means 3 to the power $P_O$ of the brain wave obtained by the brain-wave spectrum integrating means 2.

Figure 3:
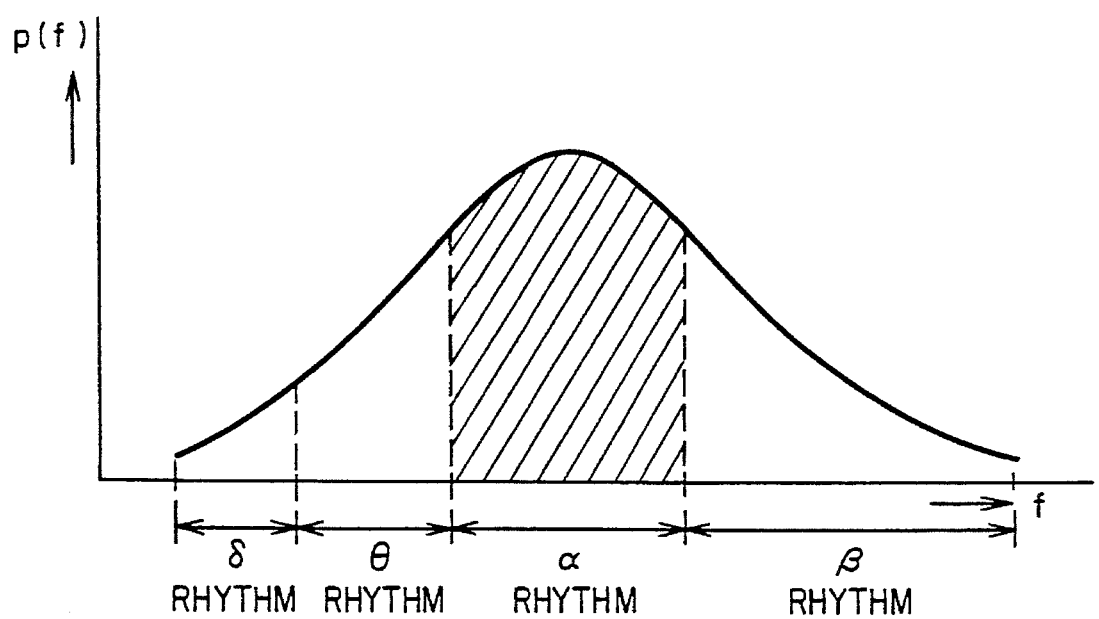
FIG. 3 is a diagram of assistance in explaining the distribution of various rhythms in a brain wave.

Since the degree of mental concentration is measured by the ratio of the power $P_\alpha$ (hatched area in FIG. 3) of the α rhythm indicating the degree of mental concentration to the power $P_O$ of the whole brain wave, measurement results are hardly affected by measuring environments, including the state of electrode penetration.

Figure 4:
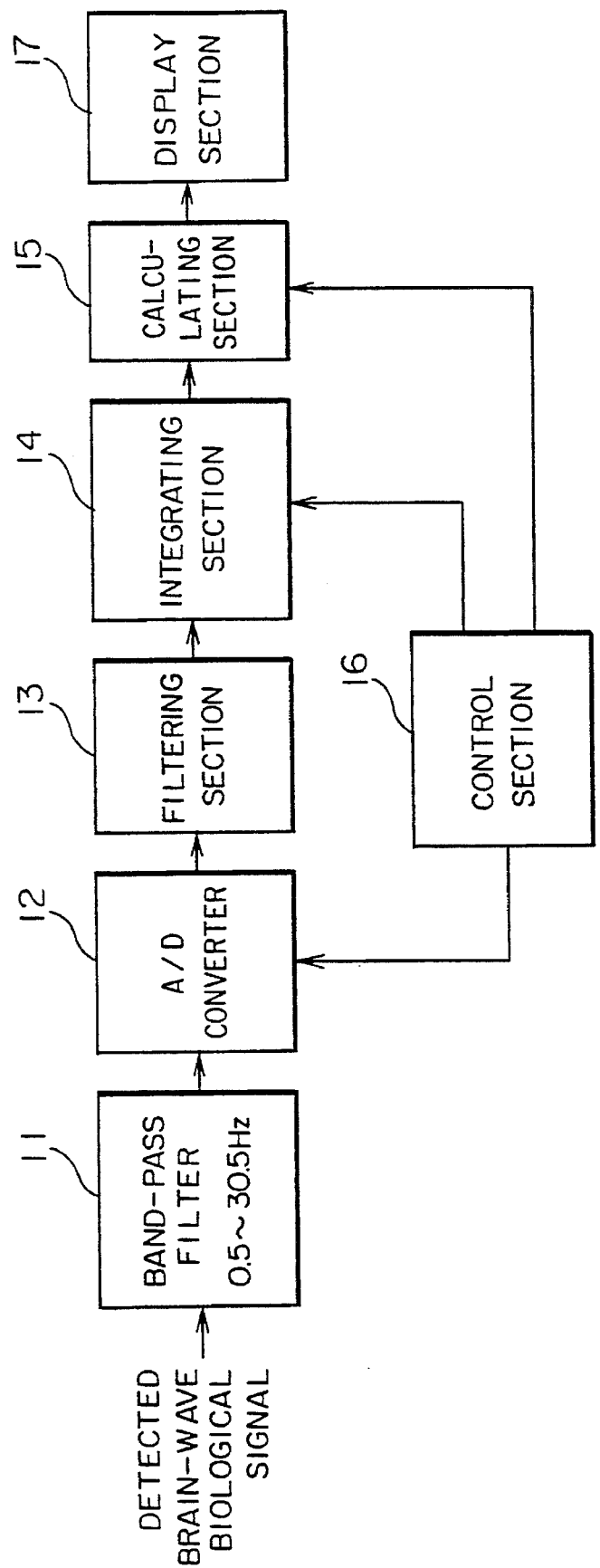
FIG. 4 is a diagram illustrating the construction of a mental-concentration apparatus embodying this invention.

FIG. 4 shows mental-concentration measuring apparatus embodying this invention.

In the figure, numeral 11 refers to a band-pass filter for preventing signal components other than frequencies from 0.5 Hz through 30.5 Hz from being passed; 12 to an A/D converter; and 13 to a filtering section for digitally extracting a signal component from a segment 0.5 Hz through 1.5 Hz, a signal component from a segment 1.5 Hz through 2.5 Hz,—a signal component from a segment 29.5 Hz through 30.5 Hz at a resolution of 1 Hz.

Numeral 14 is an integrating section for integrating the spectrum ranging from 0.5 Hz through 30.5 Hz, and the α-rhythm spectrum ranging from 7.5 Hz through 13.5 Hz, both extracted at a resolution of 1-Hz by the filtering section 13 to obtain the power $P_O$ of the brain wave and the power $P_a$ of the α rhythm as expressed by equations (1) and (2); 15 refers to a calculating section for calculating the ratio of the α-rhythm power $P_a$ obtained by the integrating section 14 to the brain-wave $P_O$; 16 to a control section; and 17 to a display section, respectively.

Figure 5:
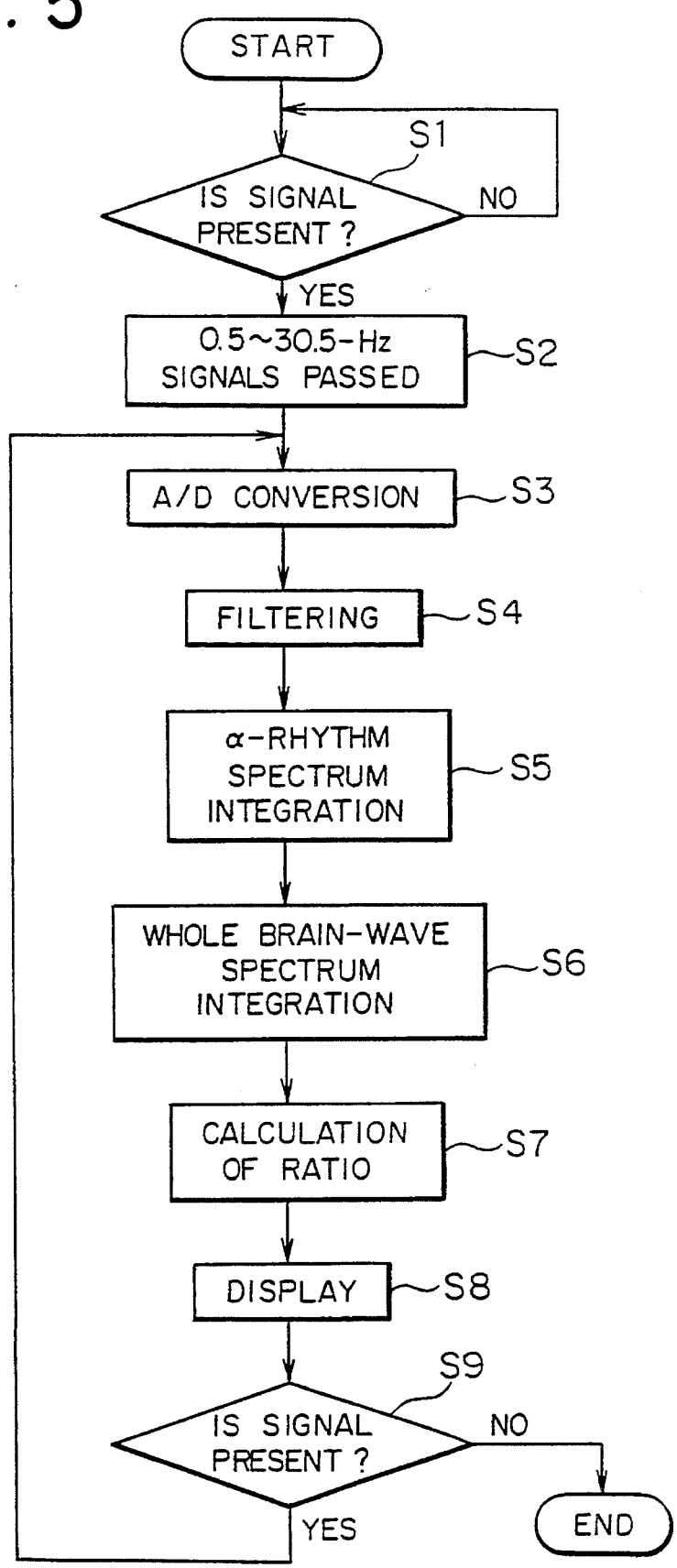

Next, the operation of FIG. 4 will be described, referring to a flow chart of an embodiment shown in FIG. 5.

When the detected biological signal of a brain wave pretreated by a differential amplifier (not shown) is input to the band-pass filter 11 (Step S1), the band-pass filter 11 allows signal components of a band width from 0.5 Hz to 30.5 Hz to pass (Step S2). The A/D converter 12 digitizes the signal input from the band-pass filter 11 in synchronism with a timing signal from the control section 16 to transmit to the filtering section 13.

In the filtering section 13, each signal component of 1-Hz width within the range from 0.5 Hz to 30.5 Hz is extracted, as described above (Step S4). The integrating section 14 integrates the spectrum of the α-rhythm signal components in the range from 7.5 Hz to 13.5 Hz based on the 1-Hz wide signal components extracted in the filtering section 13 (Step S5), transmits the obtained α-rhythm power $P_a$ to the calculating section 15, then integrates the spectrum of the whole brain-wave signal components in the range from 0.5 Hz to 30.5 Hz to obtain the brain-wave power $P_O$ (Step S6), and transmits the brain-wave signal components $P_O$ to the calculating section 15.

The calculating section 15 calculates the ratio of the α-rhythm power $P_a$ and the brain-wave power $P_O$ from both the $P_a$ and $P_O$ sent from the integrating section 14 (Step S7), and displays the degree of concentration on the display section 17 (Step S8).

Upon completion of this one cycle, the control section 16 transmits the digitized signal data from the A/D converter 12 to the filtering section 13 (Step S9). This allows Steps S3 through S9 to be repeated.

As the digitized signal data from the A/D converter 12 is transmitted at intervals of 1 second, for example, to the filtering section 13, the degree of concentration of the subject is displayed in real time every 1 second on the display section 17.

Although description has been made in the foregoing about a signal processing method relying on a digital filter, the same processing can be carried out using an analog filter in place of the digital filter.

As described above, this invention makes it possible to accurately measure the degree of concentration of a subject in real time without being affected by measuring environments.

What is claimed is:

1. A method for measuring mental concentration of the brain, the method comprising the steps of:

detecting a brain wave signal from the brain;

forming a power spectrum from said brain wave signal;

integrating said power spectrum to determine total brain-wave power;

integrating an α-rhythm portion of said power spectrum to determine an α-rhythm power;

representing and indicating mental concentration by a ratio of said α-rhythm power to said total brain wave power.

2. A method in accordance with claim 1, wherein:

said total brain-wave power is determined by integrating said power spectrum from 0.5 Hertz to 30.5 Hertz;

said α-rhythm power is determined by integrating said power spectrum from 7.5 Hertz to 13.5 Hertz.

3. A method in accordance with claim 1, wherein:

said forming of said power spectrum is by extracting signal components from a plurality of frequency segments of said brain wave.

4. A method in accordance with claim 3, wherein:

said frequency segments are substantially 1 Hertz wide and extend from 0.5 Hertz to 30.5 Hertz.

5. An apparatus for measuring mental concentration of the brain, the apparatus comprising:

brain wave extracting means for extracting a brain wave signal from the brain and for forming a power spectrum from said brain wave signal;

integrating means for integrating said power spectrum to determine total brain-wave power and for integrating an α-rhythm portion of said power spectrum to determine an α-rhythm power;

calculation means for calculating a ratio of said α-rhythm power to said total brain wave power;

display means for representing and indicating mental concentration by said ratio of said α-rhythm power to said total brain wave power.

6. A device in accordance with claim 7, wherein:

said brain wave extracting means also separates said brain wave signal into a plurality of segments and determines a power spectrum for each of said segments.

\* \* \* \* \*